United States Patent
Mrowka et al.

(10) Patent No.: US 10,556,019 B2
(45) Date of Patent: Feb. 11, 2020

(54) HUMAN MICRORNAS FOR TREATMENT OF MALIGNANT TUMOURS

(71) Applicant: UNIVERSITÄTSKLINIKUM JENA, Jena (DE)

(72) Inventors: Ralf Mrowka, Jena (DE); Axel Gohring, Jena (DE)

(73) Assignee: UNIVERSITÄTSKLINIKUM JENA, Jena (DE)

( * ) Notice: Subject to any disclaimer, the term of this patent is extended or adjusted under 35 U.S.C. 154(b) by 0 days.

(21) Appl. No.: 15/753,976

(22) PCT Filed: Aug. 23, 2016

(86) PCT No.: PCT/EP2016/069915
§ 371 (c)(1),
(2) Date: Feb. 21, 2018

(87) PCT Pub. No.: WO2017/032776
PCT Pub. Date: Mar. 2, 2017

(65) Prior Publication Data
US 2018/0264138 A1 Sep. 20, 2018

(30) Foreign Application Priority Data

Aug. 21, 2015 (EP) .................... 15182082

(51) Int. Cl.
*C12N 15/11* (2006.01)
*A61K 48/00* (2006.01)
*C07K 14/47* (2006.01)
*C12N 15/113* (2010.01)
*A61P 35/00* (2006.01)
*C12N 15/85* (2006.01)

(52) U.S. Cl.
CPC ........ *A61K 48/005* (2013.01); *A61K 48/0016* (2013.01); *A61P 35/00* (2018.01); *C07K 14/4702* (2013.01); *C12N 15/1135* (2013.01); *C12N 15/85* (2013.01)

(58) Field of Classification Search
None
See application file for complete search history.

(56) References Cited

U.S. PATENT DOCUMENTS

2008/0050744 A1* 2/2008 Brown .................. C12N 15/111
435/6.14
2009/0239816 A1* 9/2009 Rivory ............... A61K 31/7105
514/44 R 2010/0179213 A1* 7/2010 Patrawala ............ C12N 15/113
514/44 R
2014/0088170 A1 3/2014 Shi et al.

OTHER PUBLICATIONS

Huse et al, The PTEN-regulating microRNA miR-26a is amplified in high-grade glioma and facilitates gliomagenesis in vivo, 2009, Genes & Development, 23: 1327-1337 (Year: 2009).*
Liu et al, Clinical Implications of Stem Cell Gene Oct-4 Expression in Breast Cancer, Annals of Surgery, 2011, vol. 253, 6: 1165-1171 (Year: 2011).*
Man Li et al: "microRNA-299-3p inhibits laryngeal cancer cell growth by targeting human telomerase reverse transcriptase mRNA" Molecular Medicine Reports, Jan. 30, 2015, abstract.
Liu L Et Al: "microRNA-195 promotes apoptosis and suppresses tumorigenicity of human colorectal cancer cells", Biochemical and Biophysical Research Communications, Elsevier, Amsterdam , NL, vol. 400, No. 2, Sep. 17, 2010, pp. 236-240.
Gao Ling Et Al: "miR-335 functions as a tumor suppressor in pancreatic cancer by targeting OCT4", Tumor Biology, Karger, Basel, CH, vol. 35, No. 8, May 24, 2014, pp. 8309-8318.
Rong Yin et al: "microRNA-145 suppresses lung adenocarcinoma-initiating cell proliferation by targeting OCT4", Oncology Reports, Apr. 7, 2011, 1747-1754.
Y-D Wang Et Al.: "OCT4 promotes tumorigenesis and inhibits apopstosis of cervical cancer cells by miR-125b/BAK1 pathway", Cell Death and Disease, vol. 4, No. 8, Aug. 1, 2013, p. e760.
Jiaxin Lin Et Al: "MiR-26b/KPNA2 axis inhibits epithelial ovarian carcinoma proliferation and metastasis through downregulating OCT4", Oncotarget, vol. 6, No. 27, Jun. 8, 2015, pp. 23793-23806.
Thorsen S B Et Al: "The therapeutic potential of MicroRNAs in cancer", Cancer Journal, Jones and Bartlett Publishers, US, vol. 18, No. 3, May 1, 2012, pp. 275-284.
Xiaohui Tan et al., "Abstract 3062: miR-671-5p promotes epithelial to mesenchymal transition by downregulating FOXM1 expression in breast cancer," Cancer Research 75 (15 Supp): p. 3062 (2015) (16 pages).
Barbagallo et al., "Dysregulated miR-671-5p / CDR1-AS / CDR1 / VSNL1 axis is involved in glioblastoma multiforme" Oncotarget 7: 4746-4759 (2015).
Yu et al.,"miR-671 promotes prostate cancer cell proliferation by targeting tumor suppressor SOX6" European J. of Pham. 823: 65-71 (2018).
Shi and Jin, "Role of Oct4 in maintaining and regaining stem cell pluripotency," Stem Cell Research & Therapy 2010, 1:39 (9 pages).

* cited by examiner

*Primary Examiner* — Ekaterina Poliakova-Georgantas
(74) *Attorney, Agent, or Firm* — JMB Davis Ben-David

(57) ABSTRACT

The invention relates to a nucleic acid molecule for use in a method of treatment of cancer. The nucleic acid molecule comprises a sequence selected from SEQ ID NO 001 to SEQ ID NO 038. The nucleic acid molecules provided are not provided for the treatment of laryngeal cancer.

Figure 1:
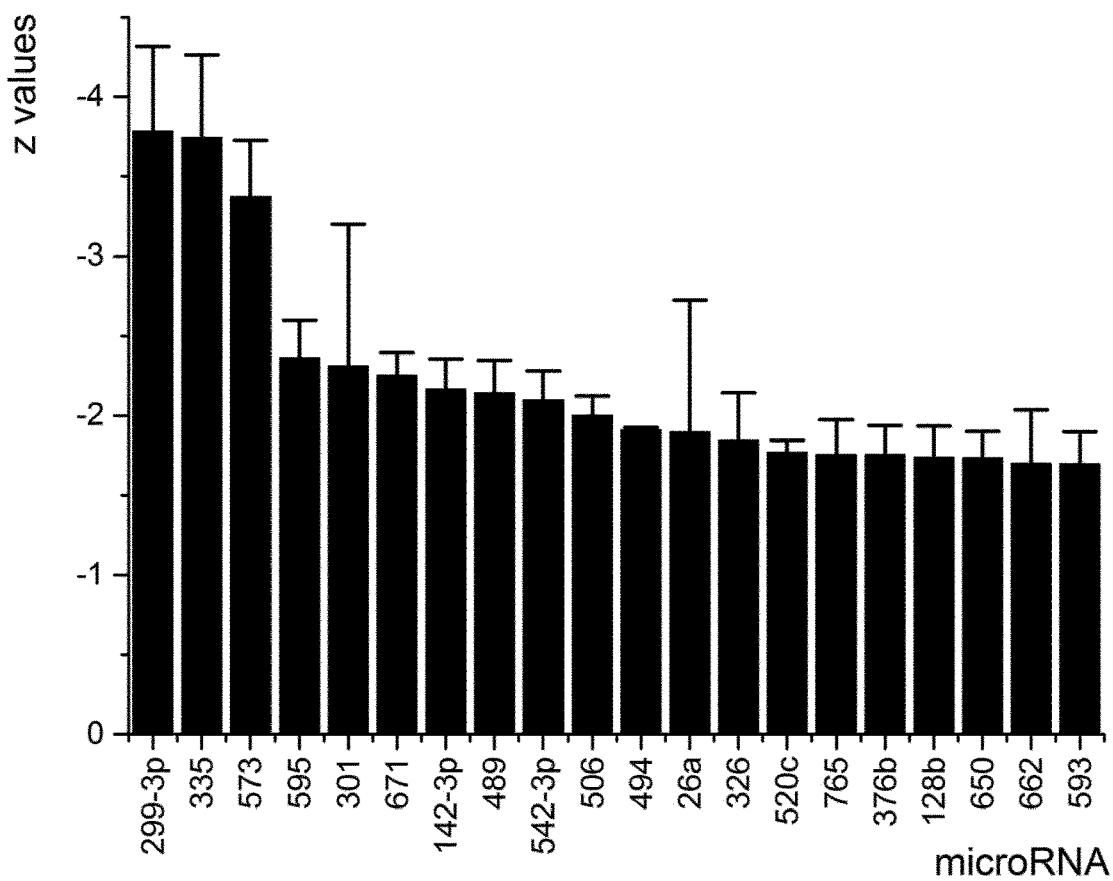

4 Claims, 8 Drawing Sheets
Specification includes a Sequence Listing.

HUMAN MICRORNAS FOR TREATMENT OF MALIGNANT TUMOURS

CROSS-REFERENCE TO RELATED APPLICATIONS

This is the U.S. National Stage of International Application No. PCT/EP2016/069915 filed Aug. 23, 2016, which was published in English under PCT Article 21(2), and which in turn claims the benefit of European Patent Application No. 15182082.6 filed Aug. 21, 2015.

FIELD OF THE INVENTION

The present invention relates to the use of human microRNAs in the treatment of malign tumours.

BACKGROUND OF THE INVENTION

Malignant tumours belong to the top 10 leading causes of death in the upper-middle and high income countries. Malign tumour cells are characterized by their unchecked growth, spreading throughout the body (migration and metastasis) and their invasion of healthy tissues. Malignant tumors overcome multiple barriers, including the extracellular matrix, before invading blood or lymph vessels on their way to spread throughout the body. In particular their ability of tissue invasion followed by establishment and growth of metastases is responsible for the lethality of cancer, because vital organs such as the lung are affected.

Commonly used compounds for the treatment of cancer such as cytostatics have an effect on all rapidly dividing cells in the body, whether they are cancerous or not. Particularly problematic is the effect on hematopoietic stem cells in the bone marrow, which leads to a rapid decline in white blood cell count and in consequence immunosuppression. This severely limits the use of cytostatics in many patients. A strategy that only targets a certain subset of cells, including cancer cells, could overcome these limitations.

According to recent research cancer cells can be thought of as cells partially retransformed into embryonic stem cells. Similar to embryonic stem cells in the uterus, they try to migrate and invade tissues able to support them (Mani et al., Cell 133, 704-715; 2008; Polyak and Weinberg, Nature Reviews Cancer 9, 265-273; 2009).

Without expression of stem cell specific genes, cancer cells lose their ability to migrate and invade other tissues. Therefore, selective ablation of stem cell specific genes in cancer cells could be a novel therapeutic opportunity. One example of a stem cell specific gene that has been linked to cancer is Oct4.

Particularly synthetic siRNA or natural microRNAs would be suitable as therapeutics. MicroRNAs are naturally occurring regulators of gene expression that represent an evolutionarily conserved gene regulatory mechanism existing in invertebrates and vertebrates. A variety of microRNAs are involved in the support of stem cells or in the initiation of stem cell differentiation into tissue specific cell types (Lichner et al., 2011, Differentiation 81, 11-24; Lüningschrör et al., 2012, Stem Cells 30, 655-664). Interestingly, some of these microRNAs are also associated with cancer.

The problem underlying the present invention is to provide microRNAs suitable for the treatment of malign tumour cells. This problem is solved by the subject-matter of the independent claims.

SUMMARY OF THE INVENTION

The inventors identified nineteen microRNAs that target the stem cell specific gene Oct4 and are suitable to inhibit Oct4 (POU5F1; UniProt Q01860) expression. Treatment of cancer cells in vitro with microRNA-299-3p results in dramatically reduced invasiveness of the cancer cells and induction of apoptosis in the cancer cells. Comparison with a microRNA known to target Oct4 (miRNA-335) surprisingly revealed that microRNA-299-3p is more potent in the reduction of invasiveness of cancer cells and additionally causes the induction of apoptosis in the cancer cells.

According to a first aspect of the invention a nucleic acid molecule for use in a method of treatment of cancer is provided, with the proviso that the cancer is not laryngeal cancer. The nucleic acid molecule is characterized by, or essentially consists of, a sequence selected from SEQ ID NO 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037 and 038.

According to a second aspect of the invention, a pharmaceutical composition for use in a method of treatment of cancer is provided, with the proviso that the cancer is not laryngeal cancer. The pharmaceutical composition comprises a nucleic acid molecule characterized by or consisting of a sequence selected from SEQ ID NO 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037 and 038.

A third aspect of the invention relates to a compound for use in a method for prevention or treatment of a disease that can be treated, prevented, modulated or ameliorated by the inhibition of Oct4 expression. The compound is selected from a nucleic acid molecule characterized by or consisting of a sequence selected from SEQ ID NO 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037 and 038.

A fourth aspect of the invention relates to a method for regulating Oct4 expression in a subject in need thereof. The method comprises administering an effective amount of a nucleic acid molecule characterized by a sequence selected from SEQ ID NO 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037 and 038.

According to a fifth aspect of the invention, a method for the activation of apoptosis in cancer cells in a subject in need thereof is provided. The method comprises administering an effective amount of a nucleic acid molecule characterized by a sequence selected from SEQ ID NO 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037 and 038.

A sixth aspect of the invention provides a recombinant expression vector comprising, or encoding, the nucleic acid sequence according to the first aspect of the invention.

Terms and Definitions

In the context of the present specification, the term microRNA is used in its meaning known in the art of cell biology and biochemistry; it refers to small non-coding RNA molecules that are typically about 22 nucleotides long, are genome-coded and function as natural occurring regulators of gene expression. They silence gene expression post-transcriptionally by binding to 3'-untranslated regions (3'UTR) of messenger RNAs. The term microRNA is used interchangeably with the terms miRNA or miR. Animal or human microRNAs are initially transcribed from the genome as part of a much longer (up to several hundred nucleotides) primary transcript termed a primary miRNA (pri-miRNA). The pri-miRNA is processed by the enzyme Drosha, which excises an approximately 60-125 nucleotides long hairpin RNA called the precursor miRNA (pre-miRNA). Processing of the pre-miRNA to the mature microRNA is performed by the enzyme Dicer, resulting in a typically 22 nucleotide long microRNA.

In the context of the present specification, the term nucleotides is used in its meaning known in the art of cell biology and biochemistry; it refers to nucleic acid molecule building blocks, oligomers of which are capable of forming selective hybrids with DNA/RNA oligomers on the basis of base pairing. The term "nucleotides" in this context includes the classic ribonucleotide building blocks adenosine, guanosine, uridine, cytidine and the classic deoxyribonucleotides deoxyadenosine, deoxyguanosine, thymidine, deoxyuridine and deoxycytidine. The hybridizing sequence may be composed of any of the above nucleotides, or mixtures thereof. Nucleotide sequences either for RNA or DNA are given in one letter codes using the abbreviations known in the art (A: adenosine; G: guanosine; C: cytidine; T: thymidine and U: uridine), with N referring to any nucleotide.

Where reference is made to a DNA sequence, such as a expression plasmid, containing or comprising a sequence given in RNA notation (containing U instead of T), it is understood that the comprised sequence is indeed a DNA sequence showing T nucleosides in the place of the U positions of the RNA sequence referenced.

In the context of the present specification, the term recombinant is used in its meaning known in the art of cell biology and molecular genetics; it refers to a particular nucleic acid (DNA or RNA) that is the product of various combinations of cloning, restriction, polymerase chain reaction (PCR) and/or ligation steps resulting in a construct having a structural coding or non-coding sequence.

In the context of the present specification, the term virus-like particle is used in its meaning known in the art of cell biology and virology; it refers to a non-infectious virus or viral scaffold comprising no viral genetic material. Virus-like particles may consist of viral structural proteins such as capsid proteins, wherein these proteins can be heterologous expressed and are able to self-assemble to the virus-like particle.

In the context of the present specification, the term antibody is used in its meaning known in the art of cell biology and immunology; it refers to glycoproteins comprising at least two heavy (H) chains and two light (L) chains inter-connected by disulfide bonds. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component of the classical complement system. Antibodies directed against antigens only occurring in specific tissues are referred to as tissue specific antibodies in the context of the present specification.

DETAILED DESCRIPTION OF THE INVENTION

According to a first aspect of the invention, a nucleic acid molecule for use in a method of treatment of cancer is provided, with the proviso that the cancer is not laryngeal cancer. The nucleic acid molecule comprises or consists of a sequence selected from SEQ ID NO 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037 and 038.

Nucleic acid sequences for the genomic region or primary-microRNA encoding the precursor-microRNA or the mature microRNA can easily be retrieved by the person skilled in the art from commonly available databases such as Mirbase (http://www.mirbase.org). In certain embodiments according to all aspects of the invention, the genomic sequence or the primary microRNA sequence may be used instead of the corresponding precursor-microRNA or mature microRNA sequence.

In certain embodiments, the nucleic acid molecule for use in a method of treatment of cancer is selected from SEQ ID NO 001 and SEQ ID NO 002.

In certain embodiments, the nucleic acid molecule is characterized by, or consists of, the sequence of SEQ ID NO 002.

In certain embodiments, the nucleic acid molecule initiates apoptosis in cancerous cells.

In certain embodiments, the cancer is selected from breast cancer, fibrosarcoma and teratocarcinoma.

According to a second aspect of the invention, a pharmaceutical composition for use in a method of treatment of cancer is provided, wherein the cancer is not laryngeal cancer. The pharmaceutical composition comprises a nucleic acid molecule comprising a sequence selected from SEQ ID NO 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037 and 038.

In certain embodiments, the pharmaceutical composition comprises a nucleic acid molecule that comprises, or consists of, a sequence selected from SEQ ID NO 001 to SEQ ID NO 002.

In certain embodiments, the pharmaceutical composition comprises a nucleic acid molecule that comprises, or consists of, the sequence of SEQ ID NO 002.

In certain embodiments, the pharmaceutical composition additionally comprises polyethylene glycol coupled liposomes, tissue specific antibodies, virus-like particles, cell-penetrating peptides (CPP), penetrating metal particles, magnetic particles, photo activated penetrating particles, chemically activated penetrating particles, enzymatically activated penetrating particle. In general, every method known to the person skilled in the art that can be used to introduce microRNAs into tissues can be used to exercise this invention.

According to a third aspect of the invention, a compound for use in a method for prevention or treatment of a disease that can be treated, prevented, modulated or ameliorated by the inhibition of Oct4 expression is provided. The compound is selected from a nucleic acid molecule comprising a sequence selected from SEQ ID NO 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037 and 038.

In certain embodiments, the nucleic acid molecule for use in a method for prevention or treatment of a disease that can be treated, prevented, modulated or ameliorated by the inhibition of Oct4 expression comprises, or consists of, a sequence selected from SEQ ID NO 001 to SEQ ID NO 002.

In certain embodiments, the nucleic acid molecule for use in a method for prevention or treatment of a disease that can be treated, prevented, modulated or ameliorated by the inhibition of Oct4 expression comprises, or consists of, the sequence of SEQ ID NO 002.

According to a fourth aspect of the invention, a method for regulating Oct4 expression in a subject in need thereof is provided. The method comprises administering an effective amount of a nucleic acid molecule that consists of or comprises a sequence selected from SEQ ID NO 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037 and 038 to the subject.

In certain embodiments, the nucleic acid molecule for use in a method for regulating Oct4 expression in a subject in need thereof comprises, or consists of, a sequence selected from SEQ ID NO 001 and SEQ ID NO 002.

In certain embodiments, the nucleic acid molecule for use in a method for regulating Oct4 expression in a subject in need thereof comprises, or consists of, the sequence of SEQ ID NO 002.

According to a fifth aspect of the invention, a method for the activation of apoptosis in cancer cells in a subject in need thereof is provided. The method comprises administering an effective amount of a nucleic acid molecule comprising or consisting of a sequence selected from SEQ ID NO 001, 002, 003, 004, 005, 006, 007, 008, 009, 010, 011, 012, 013, 014, 015, 016, 017, 018, 019, 020, 021, 022, 023, 024, 025, 026, 027, 028, 029, 030, 031, 032, 033, 034, 035, 036, 037 and 038.

In certain embodiments, the nucleic acid molecule for use in a method for the activation of apoptosis in cancer cells comprises, or consists of, a sequence selected from SEQ ID NO 001 to SEQ ID NO 002.

In certain embodiments, the nucleic acid molecule for use in a method for the activation of apoptosis in cancer cells comprises, or consists of, the sequence of SEQ ID NO 002.

According to a sixth aspect of the invention, a recombinant expression vector comprising, or encoding, the nucleic acid sequence according to the first aspect of the invention is provided.

In certain embodiments, the nucleotide sequence is operably linked to a promoter, particularly a promoter operable in a eukaryotic cell, more particularly a promoter operable in a human cell.

In certain embodiments, the promoter is an inducible promoter.

Wherever alternatives for single separable features such as, for example, a microRNA sequence is laid out herein as "embodiments", it is to be understood that such alternatives may be combined freely to form discrete embodiments of the invention disclosed herein.

The invention is further illustrated by the following examples and figures, from which further embodiments and advantages can be drawn. These examples are meant to illustrate the invention but not to limit its scope.

SHORT DESCRIPTION OF THE FIGURES

FIG. 1 shows twenty microRNAs that interact with the 3'UTR of Oct4. Bars represent z-values. The preceding z-transformation of signal values of *Renilla* luciferase (reporter enzyme) and Firefly luciferase (normalization enzyme, for cell number) makes a standardization of all results for the whole library possible. Error bars are standard error of means (n=3).

Figure 2:
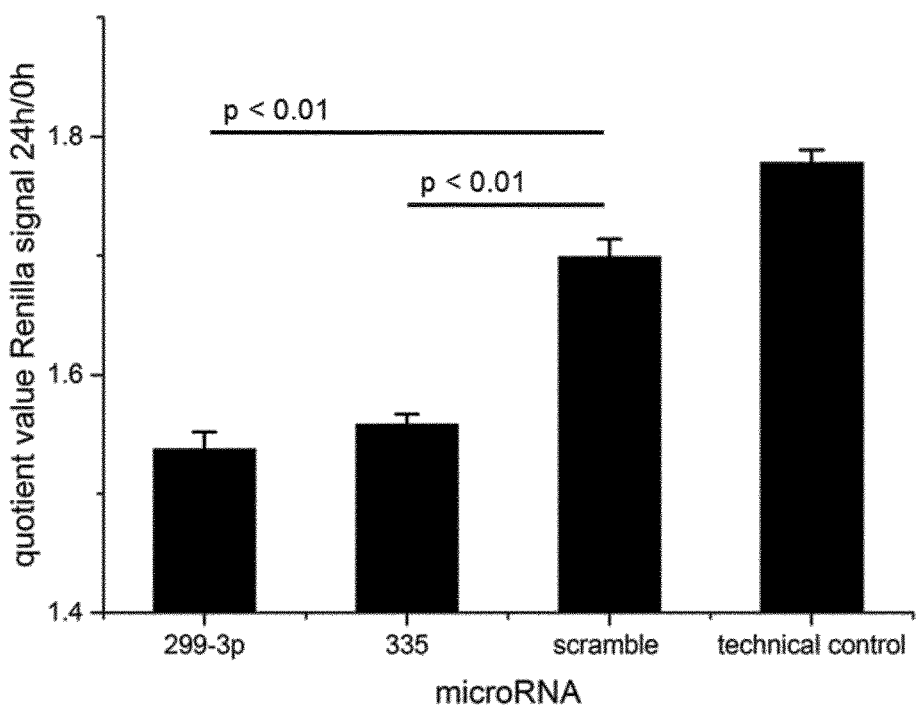

FIG. 2 shows repression of Oct4 expression by microRNAs miRNA-299-3p and miRNA-335. NCC-IT based cells with a genomically integrated Oct4-responsive reporter construct were transfected with the indicated miRNAs. Oct4-reporter signal (Firefly luciferase) corresponding to the expression of Oct4 was measured after 24 hours.

Figure 3:
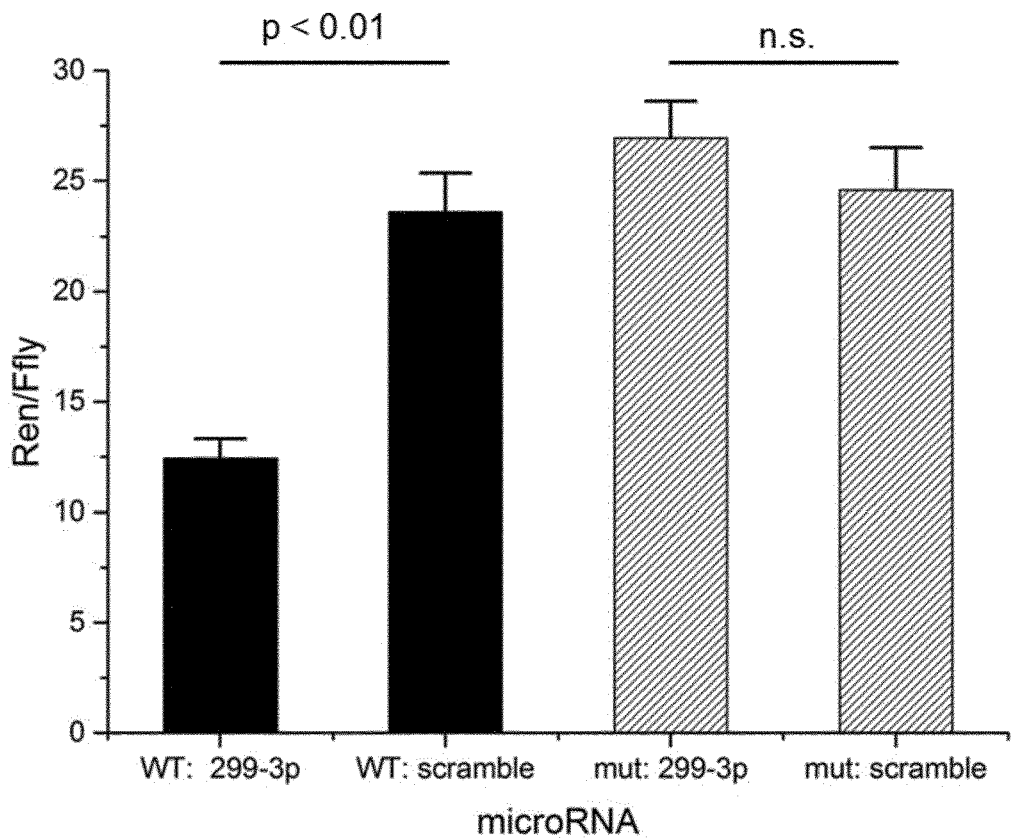
Figure 3:
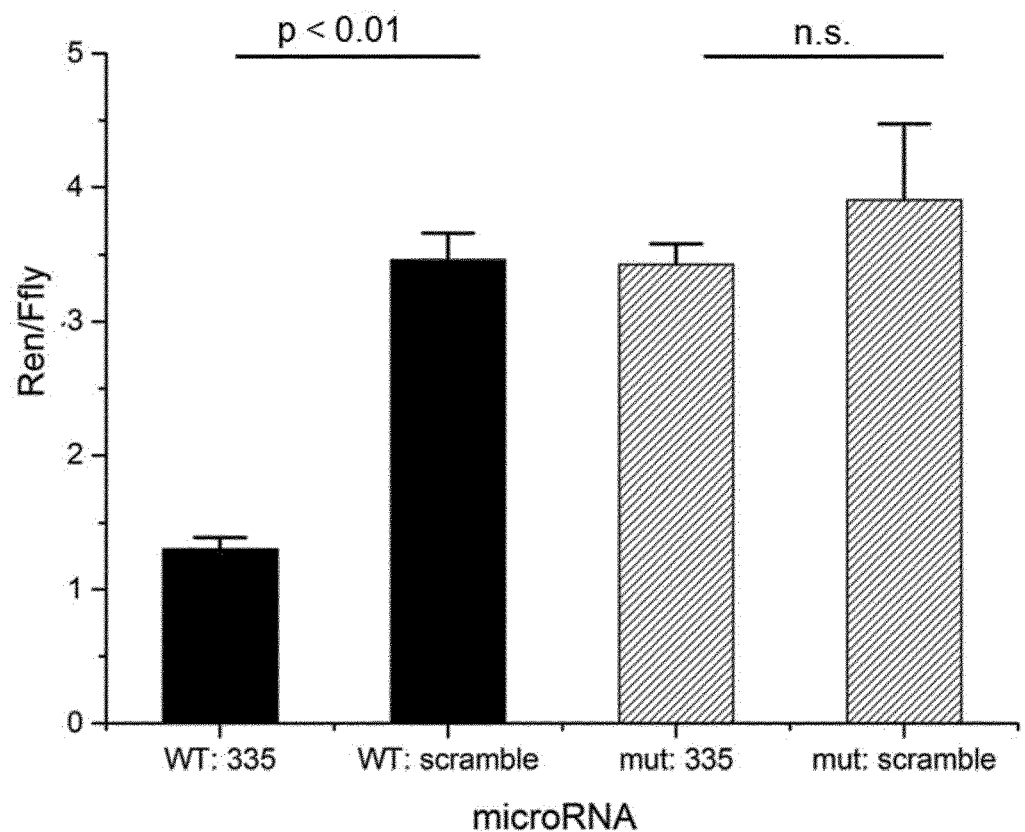

FIG. 3 shows the disruption of Oct4mRNA-miRNA hybridization by mutation of the respective binding sites for microRNA-299-3p and microRNA-335. WT: wild type, mut: mutated binding site, scramble: non-human microRNA sequence (negative control). Error bars are standard error of means (n=6).

Figure 4:
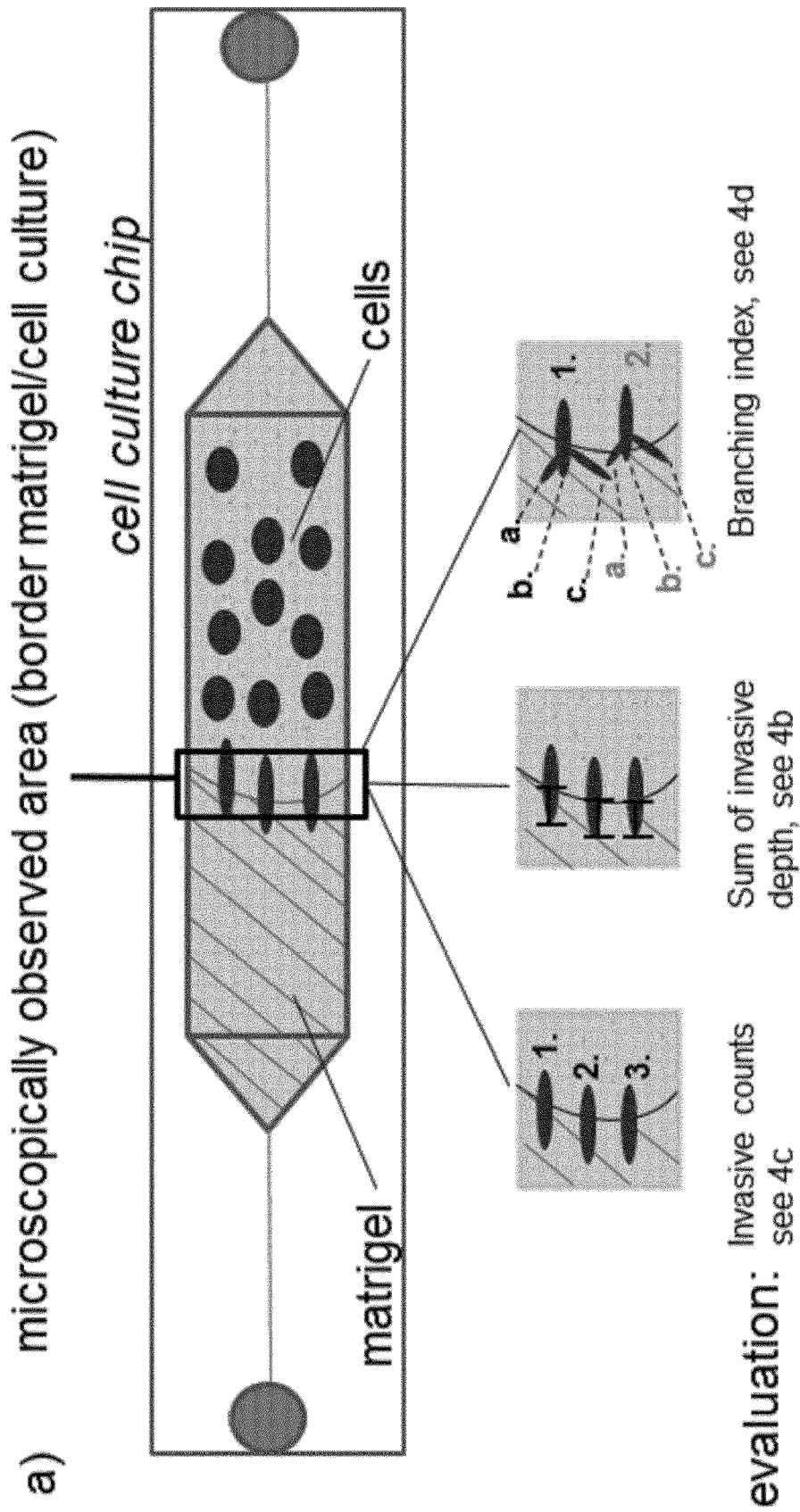
Figure 4:
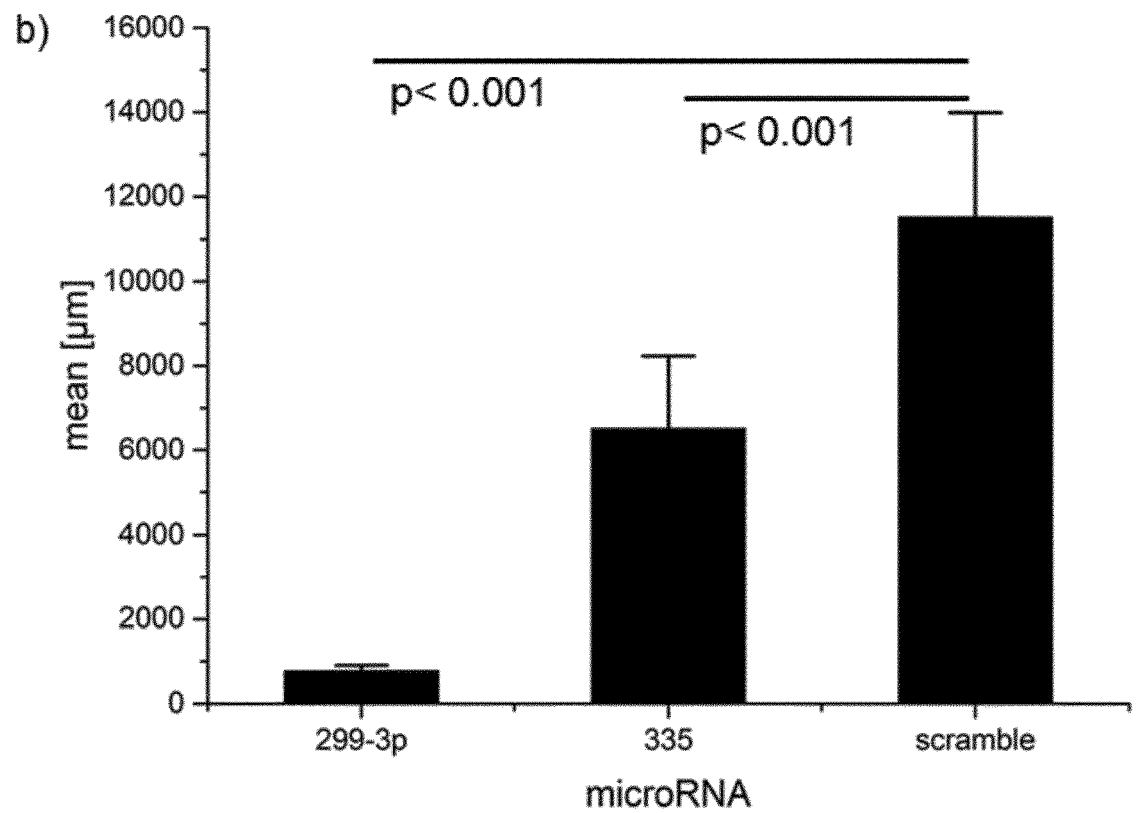
Figure 4:
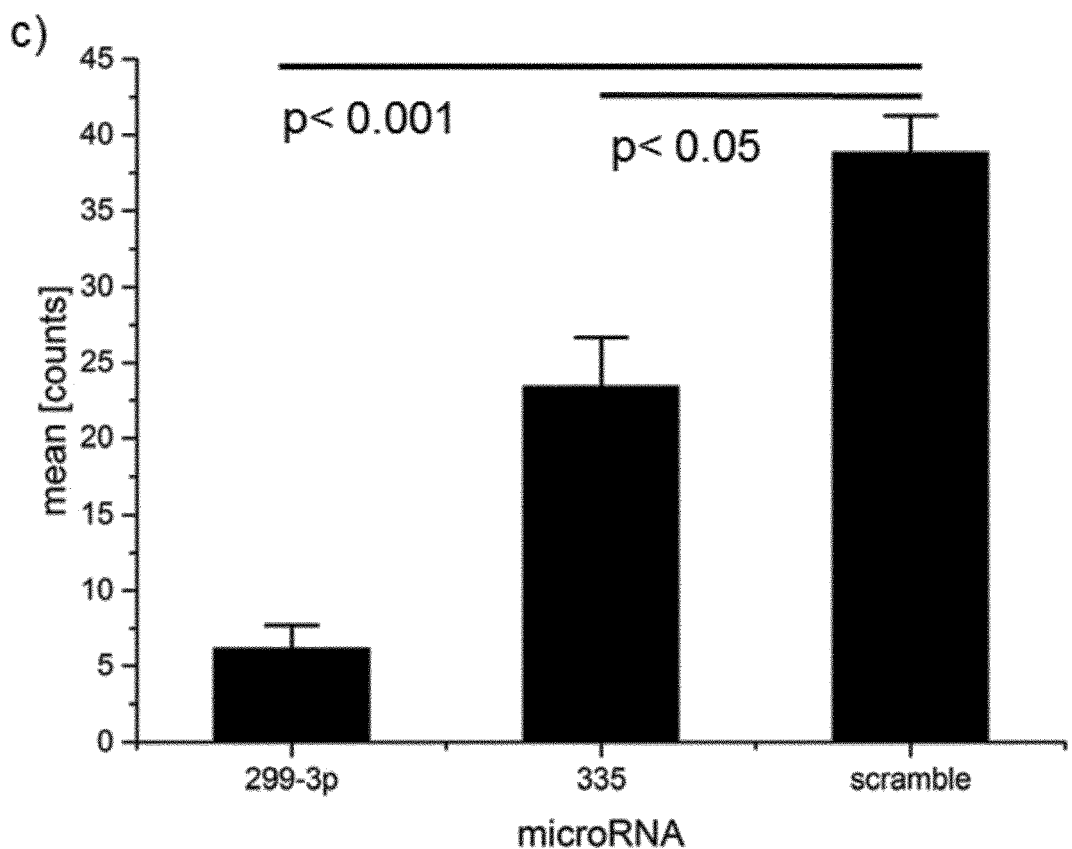
Figure 4:
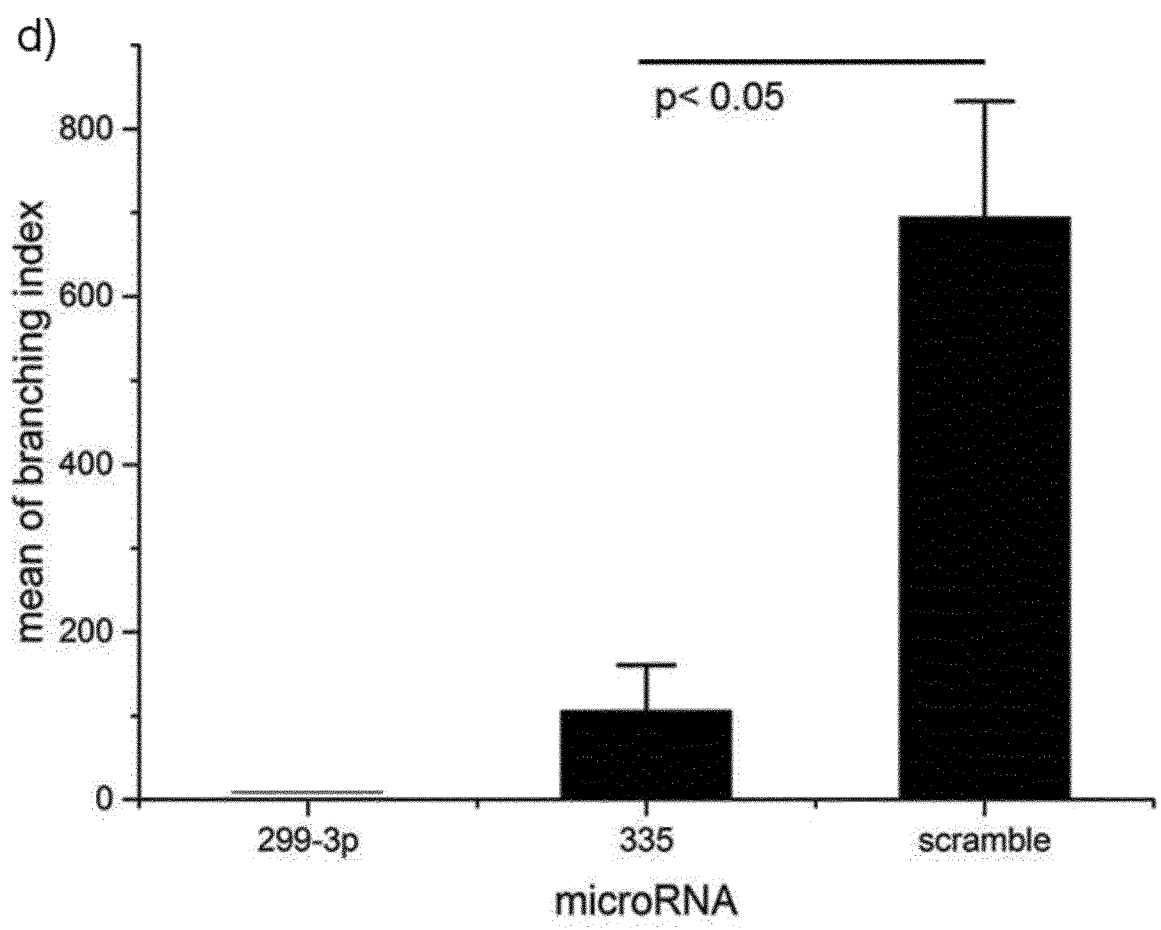

FIG. 4 shows the effect of microRNA-299-3p and microRNA-335 on the capability for invasion of MDA-MB-231 breast cancer cells. a) schematic overview of the used invasion assay; inhibiting effect of miRNA-299-3p and miRNA-335 on the invasive behaviour of MDA-MB-231 breast cancer cells. Both miRNAs reduced the b) invasion depth in μm, c) number of invasive cells and d) branching of invading cells. Error bars are standard error of means (n=11/9/7). Statistical significance was tested with t-test. No branching was observed after stimulation with microRNA-299-3p.

Figure 5:
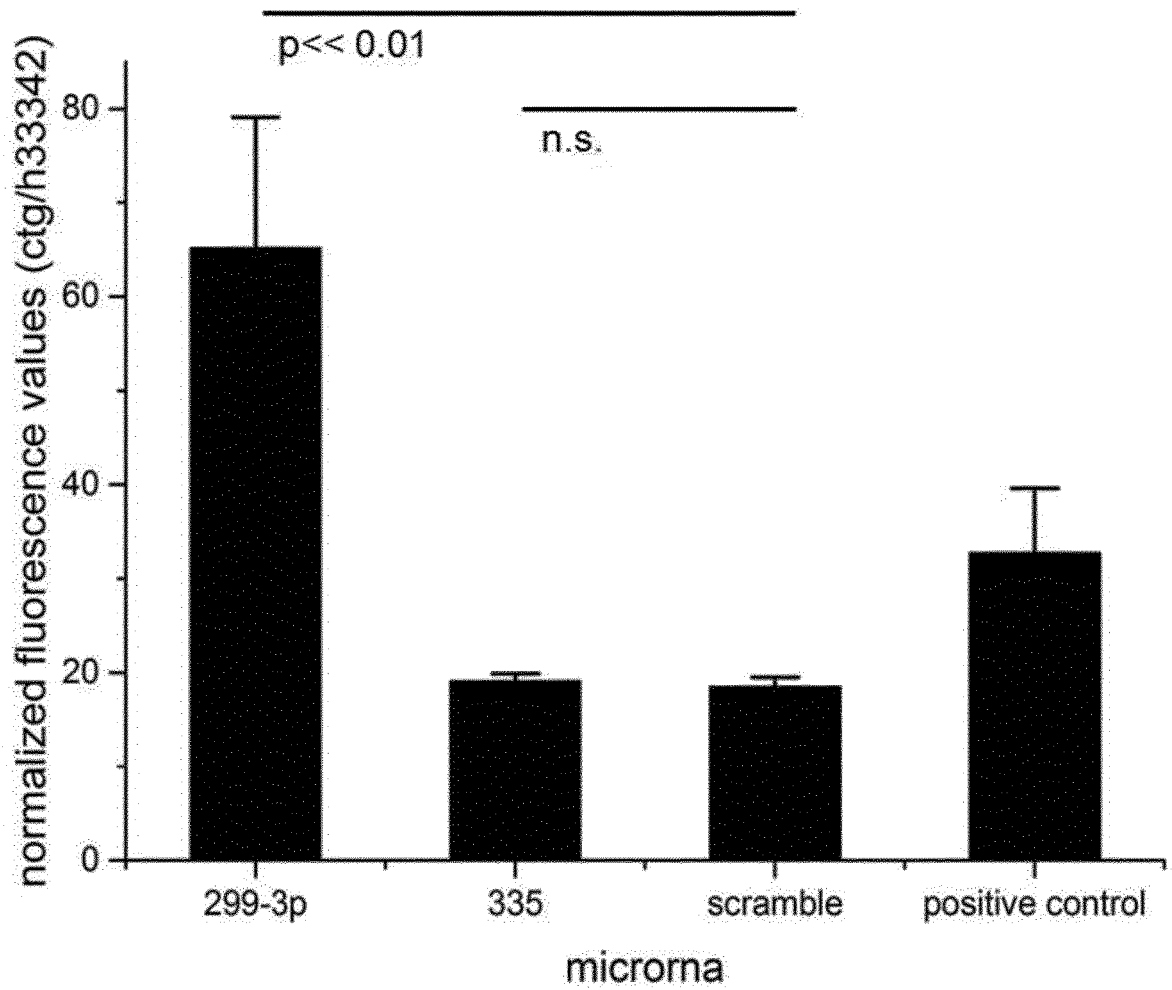

FIG. 5 shows that microRNA-299-3p induces apoptosis in MDA-MB-231 breast cancer cells. Cytotoxicity assays were performed with CellToxGreen-dye as described in the examples. scramble: non-human microRNA sequence (negative control). Error bars are standard error of means (n=10/9/10/5). Statistical significance was tested with H-test (Kruskal-Wallis-Test).

Figure 6:
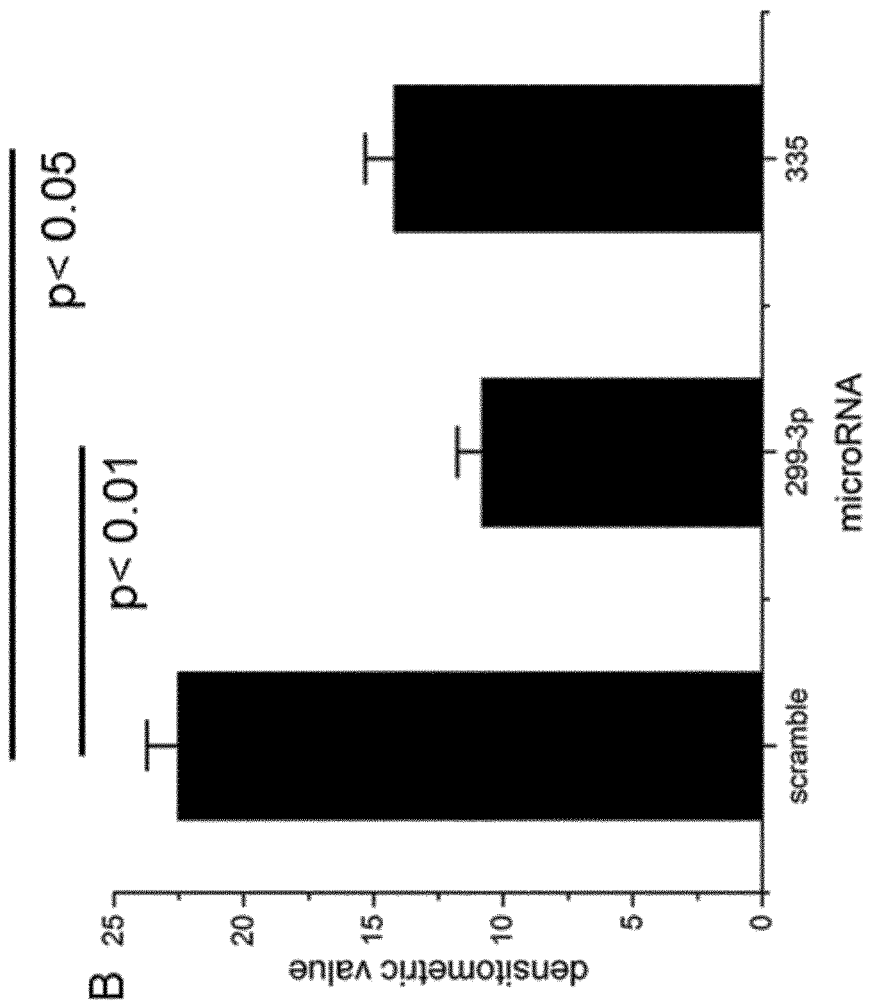
Figure 6:
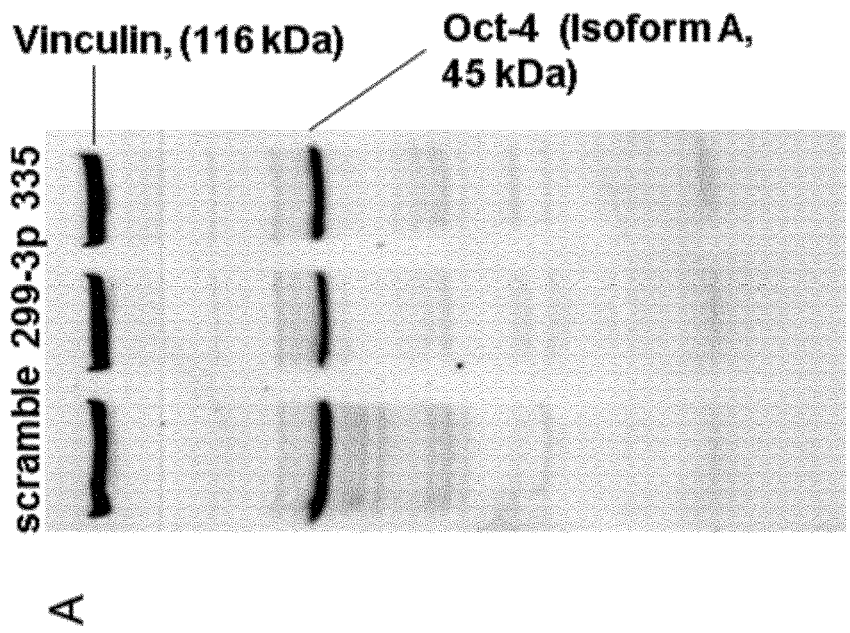

FIG. 6 shows the reduction of OCT4 protein content by microRNA-299-3p and microRNA-335. A) Immunoblotting analysis of the transcription factor Oct4 (isoform A) in NCC-IT-Oct4 cells transfected with either miR-299-3p, miR-335 or a non-human miR used as negative control (scramble). B) Densitometric analysis of Oct4 expression (isoform A) in NCC-IT-Oct4 cells transfected with either miR-299-3p, miR-335 or a non-human miR used as negative control (scramble). Error bars are standard error of means (n=4). Statistical significance was tested with H-test (Kruskal-Wallis-Test).

Figure 7:
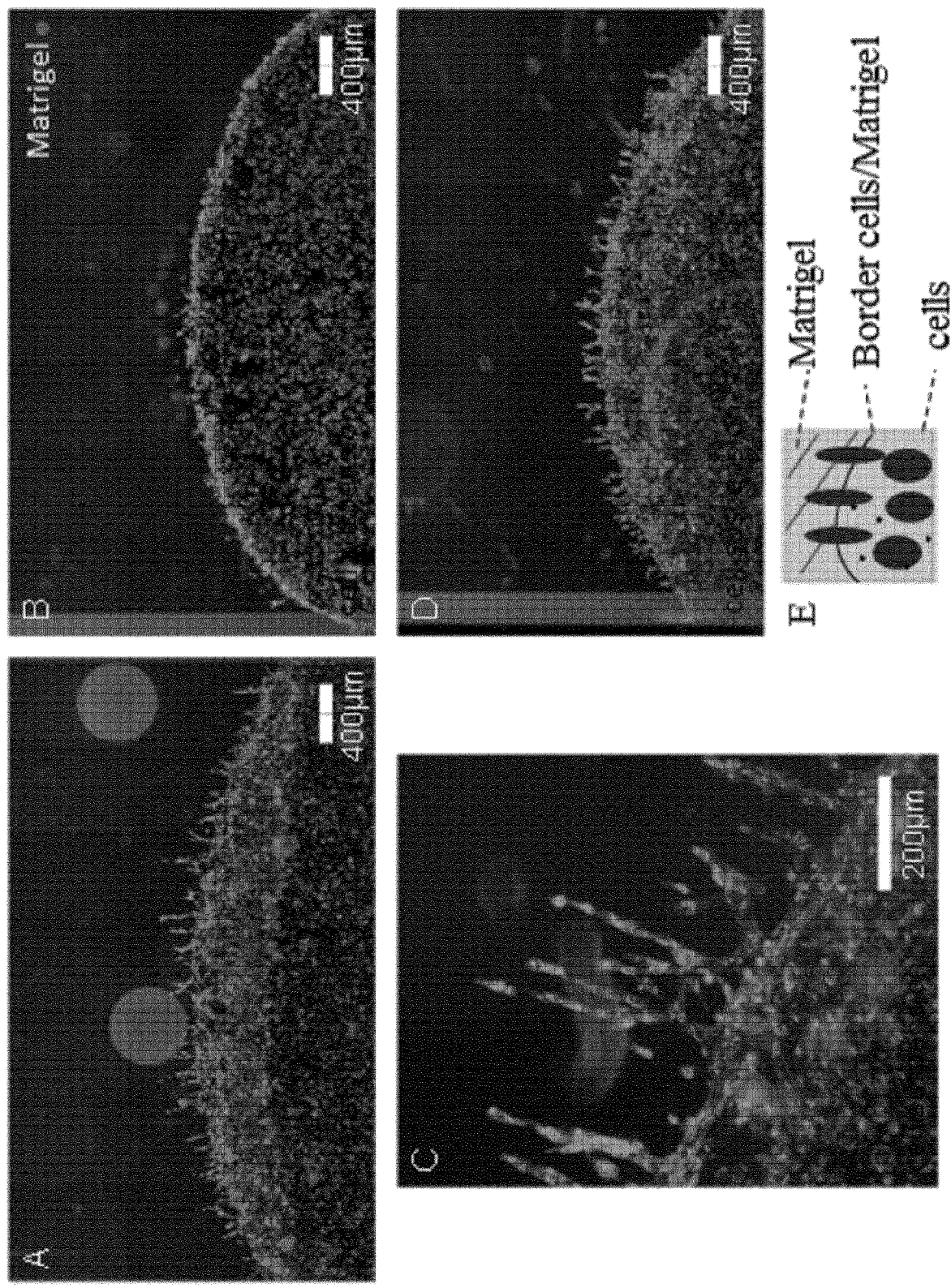

FIG. 7 shows photographs taken from the invasion assays described in FIG. 4. MDA-MB-231 cells were transfected with different pre-miRs A) scramble (negative control), B) miR-299-3p, C) magnification of A), D) miR-335 and E) schematic representation. Object lenses used: 10× for A), B) and D) and 40× for C).

EXAMPLES

Example 1 (Identification of Oct4 Interacting and Modulating miRNAs)

A high-throughput detection method was utilized to identify human miRNAs that interact with Oct4.

Cloning of Oct4-3'UTR Vector

The 3'UTR sequence of Oct4 was amplified from a human genomic template by PCR and cloned into a fusion plasmid with the reporter genes for Firefly and *Renilla* luciferase controlled by a CMV promoter. The fusion plasmid called "pc5/Psi" was cloned previously by using parts of pcDNA5/FRT (Invitrogen) and psiCHECK-2 (Promega, catalog C8021). *Renilla* luciferase was coupled with the 3'UTR serving as reporter gene, and Firefly luciferase served as cell number control.

Stable Transfection of HEK293-FRT Cells by Homologous Recombination

Using the Flp-In system (Invitrogen), HEK293 cells were transfected with the 3'UTR dual luciferase vectors. Both the cells and the plasmids possessed a Flippase Recognition Target site (FRT). The Flippase gene was provided by an additional vector called pOG44 (Invitrogen). The enzyme recognizes the FRTs, cuts the DNA and ligates the 3'UTR vectors with the genomic site. The resulting transgenic HEK293 cells were thus isogenic and could be selected by hygromycin due to the resistance gene of the vector. The cellular genomic transgene was verified by PCR.

For the preparation of the transfection solution 100 µl of Opti-MEM (Gibco), 2 µg of the pc5/Psi vector and 18 µg of pOG44 were mixed and combined with a mix of 100 µl of Opti-MEM and 10 µl Roti-Fect (Roth). The combined solution was incubated for at least 15 min at ambient temperature.

After 24 hours, the transfection medium was replaced by fresh complete medium (DMEM based, Gibco), and the cells were cultured for another day. Next, cells were splitted 1:5 and after growth of the cells, 10 ml of complete medium with 300 µg/ml hygromycin B were then added to the cells. After 24 hours, the medium was replaced by 10 ml complete medium supplemented with 100 µg/ml hygromycin. The cells were further cultured for at least a week.

microRNA and Oct4 Interaction and Validation

The pre-microRNA library provided by Ambion contained 477 individual human microRNAs distributed on six 96-well plates. The manufacturer's term pre-microRNA (double stranded DNA w/o stem-loop structure) must not be confused with the scientific concept (stem loop DNA). The absolute amount per miRNA species was 250 pmol. Using a multichannel pipette, the nucleotides were dissolved in 50 µl RNase-free water to achieve a concentration of 5 pmol/µl. The plates were then cryopreserved (−20° C.).

In preparation for the transfection, the miRNA solutions were dispensed into luminometer plates (Greiner; 3 pmol/5 µl) using a cell culture robot (CyBio Selma) under sterile conditions.

For the transfection, the plates were thawed and centrifuged briefly to collect the liquid in the ground. Using the luminometer (Labsystems), 15 µl of transfection solution (14.8 µl of Opti-MEM, 0.2 µl Lipofectamine RNAiMAX) were injected into each well. The plates were incubated for at least 15 min at 20° C. in the dark in order to achieve a complete complexation of liposomes and nucleic acids.

Then, 100 µl of cell suspension, always containing 12,500 cells, were injected into each well with the luminometer after previous sterilization of the injector hoses.

After incubation of the plates for 24 hours at 37° C. and 5% $CO_2$ the cells were lysed with 20 µl of 1:5 diluted passive lysis buffer (Promega) and shaked rigorously. In order to perform the luciferase assay later, the plates were frozen at −20° C.

No later than three days after cryopreservation, the luciferase activity in the cell lysates was determined using 100 µl Firefly and *Renilla* buffer each. The luminometer was programmed to measure with a delay of six seconds after injection and a duration of ten seconds.

The obtained luminescence values were standardized using a z-transformation to make the signals of all the samples comparable. This standardization relates the mean and standard deviation of the entire 96-well luminometer plate values.

MicroRNA Interaction with the 3'UTR of Oct4

In FIG. 1 the twenty most strongly interacting miRNAs are shown. The strongest interaction (note that z-values are always negative and the lower the value the stronger the interaction) was found for the miRNA-299-3p. The second best miRNA was miRNA-335, which was already reported to interact with Oct4 and therefore represents a valuable positive control demonstrating the validity of the used assay.

Example 2: Regulation of Oct4 Expression by miRNAs

An Oct4 reporter system established in NCC-IT cells was used to identify effects of miRNAs on Oct4 expression levels.

Long-Term Measurement of miRNA Interaction with Lentiviral Reporter System

In order to investigate the effect of miR-299-3p in alternative cellular systems, a NCC-IT based cell line (Teshima et al., Lab Invest. 1988 September; 59(3):328-36). with a genomically integrated HIV-derived lentiviral Oct4-reporter construct (Cignal, Qiagen) was transfected with miR-299-3p. Additionally miR-335 was used as positive control and scrambled miR as negative control, respectively.

The Oct4-reporter construct consists of an Oct4-responsive promoter sequence and the gene for the Firefly luciferase. The gene for Oct4 is expressed natively in the selected cell line Approximately 12,500 cells per well were transfected with 3 pmol miRNA incl. negative control (see above) in 100 µl medium (DMEM w/o phenol red, 10% FCS, 1% HEPES, 250 µM Luciferin D) in a 96-well luminometer plate.

The response of NCC-IT-Oct4 cells to miRNA stimulation was recorded over a period of 24 h in a temperature-controlled luminometer at 37° C. (Top Count, Packard).

Immunoblot Analysis

In order to investigate the effect of miR-299-3p and miR-335 on the abundance of Oct4 protein levels, around 62,500 NCC-IT-Oct4 cells were seeded into a 24-well-cell culture plate and were transfected with 0.75 µl Lipofectamine® RNAiMAX and 15 pmol premicroRNA-299-3p, -335 and the negative control in Opti-MEM® (ad 500 µl).

This procedure was twice repeated every 24 h.

A degenerative miRNA effect could be observed after 3 days by visual inspection. The cells were lysed in 40 µl urea buffer (6 M). The cell debris was removed by centrifugation. The protein content of the solution was determined using a spectrophotometer.

For the detection of Oct4 protein isoform A (45 kDa), a concentration of 10% was chosen for the polyacrylamide gel separation. Vinculin was used as a loading control. For electrophoresis, 40 µl protein solution (c=50 µg/ml) were applied.

After protein transfer, the blot membrane (PVDF) was incubated with the two primary antibody solutions (against Oct4, isoform A and B, sc-5279, Santa Cruz; each with antibody against vinculin, 4650, Cell signaling technology, 1:100,000=2 ng/ml). The blot membrane was washed and afterwards incubated with a secondary antibody solution (infrared chromophore, 35568, Thermo Fisher). The infrared signals of the hybridizing secondary antibodies were detected with a documentation tool and digitized. The signal bands in the files were obtained by densitometry measured with an Image Analyzer program (Aida).

miRNA-299-3p Regulates Oct4 Expression

The reduction of Oct4 expression is shown in FIG. 2 using the lentiviral reporter system mentioned above. Both tested microRNAs reduced the expression of Oct 4 significantly when compared to a non-human control microRNA used as negative control (scramble).

In FIG. 6 the effect of miR-299-3p and miR-335 on the abundance of Oct4 protein levels in NCC-IT-Oct4 cells is shown. Transfection with miR-335 significantly reduced Oct4 protein levels by ~40% as compared to negative control (scramble). Treatment with miR-299-3p resulted in a significant reduction of Oct4 protein levels by 55% as compared to negative control (scramble).

Example 3: Mutation of Putative Binding Site

Binding Analysis of the Interaction Between miRNA and Oct4

To investigate which area of the Oct4 3'UTR is bound by effective microRNAs, the putative binding sites were determined using the bioinformatical service TargetScan (www.targetscan.com).

The potentially binding nucleotides for both microRNAs were partially replaced in silico (FIG. 3). The two mutated 3'UTR sequences with additional restriction sites were synthesized by a service provider and afterwards cloned into the pc5/Psi dual luciferase vector.

The two plasmids with both mutated 3'UTRs of Oct4 (mut) and a pc5/Psi vector with an unaltered 3'UTR sequence (WT) serving as control were transiently transfected into HEK293. The transfection medium was added to about 500,000 cells in a 6-well plate with 2 ml medium per well. After 24 h at 37° C. and 5% $CO_2$, the cells were trypsinized and seeded in a microtiter plate luminometer (96 well plate) with a concentration of about 25,000 cells per well. The cells were transfected with miRNAs-299-3p, 335 or a negative control (scramble). After additional incubation for 24 h, the cells were lysed and the luciferase activity was determined using a luminometer.

Mutation of the Binding Site Abolishes Effect of miRNAs 299-3p and 355 on Oct4 Expression As shown in FIG. 3 mutation of the binding sites for the miRs 299-3p and 335 prevents their inhibitory effect on Oct4 expression. Whereas miR-299-3p significantly reduces Oct4 expression in unmutated control cells (WT), this effect is completely absent in cells with a mutated binding site (mut; FIG. 3 upper graph). Non-human miR used as a negative control (scramble) did not affect Oct4 expression in the wildtype or mutants, thereby demonstrating the sequence specific effect of miR-299-3p. Identical results are observed using miR-335 (FIG. 3 lower graph).

Example 4: Effect of miRNAs on Invasive Capacity of Cancer Cells

Invasion Assays

The invasion assays were performed in hydrophilized thermoplastic microfluidic chips (made of Zeonor, Fluidik 221, microfluidic ChipShop). The chamber of a chip was filled half with 50 µl matrigel (BD) containing the fluorescent dye DY-630-OH (c=100 µg/µl, Dyomics). After thermosetting of the matrigel, an additional air outlet was created with a glowing felting needle in the middle of the chamber.

The day before highly invasive breast carcinoma cells (MDA-MB 231) were transfected with premicroRNA-299-3p, 335 or negative control (scramble; 150 pmol and around 400,000 cells per well in a 6-well cell culture plate). Then, a cell suspension with a concentration of about 1000 cells/µl was injected into the other half of the chip chambers. After 48 h, the contact area of cell suspension and matrigel was photographed with a fluorescence microscope.

miR-299-3p and miR-335 Reduce Invasive Capacity of Cancer Cells

Using this assays three different parameters relating to the invasive capacity of a cancer cell can be measured, the sum of invasive depth, the number of cells that showed invasive action (invasive counts) and the branching index of invading cells.

In FIG. 4b the mean sum of invasive depths is shown for breast cancer cells transfected with either miR-299-3p, miR-335 or a non-human miR used as negative control (scramble). Whereas treatment with miR-335 almost halfed the invasive depth in comparison to the negative control, treatment with miR-299-3p almost completely abolished the invasion of cancer cells.

A similar picture can be observed regarding the number of cells that showed invasive behavior. Treatment with miR-35 reduced the number of invading cells by ~30% whereas miR-299-3p reduced the number of invading cells by more than 80%.

The number of branches invading cells can develop is associated with the aggressiveness. The branching index is calculated from the number of branched invasions multiplied with the number of branches in each event. Whereas cells treated with miR-335 have a dramatic reduction of their branching index by ~85%, cells treated with miR-299-3p practically show no branching at all.

Photographic images of invasions assays with cells treated with various miRs are provided in FIG. 7. In FIGS. 7 A) and C) cells treated with a non-human miR as negative control are shown. Treatment with miR-299-3p is shown in FIG. 7 B) and treatment with miR-335 is seen in FIG. 7 D).

Example 5: Induction of Apoptosis in Cancer Cells

Cytotoxicity Assays

MDA-MB-231 cells were pre-stained with Hoechst 33342 (bisBenzimide, as cell number control) with a concentration of 1 µg/ml dye in full RPMI 1640 medium (incl. 10% FCS and 1% Pen/Strep). After 24 h the Hoechst medium war removed and the cells were transfected with 3 pmol premiRNA-335 and -299-3p in 96-well luminometer plates. Simultaneously, the cells were stained with CellTox™ Green dye (Promega) following the manufacturer's recommendations for endpoint express protocol. After an additional 48 h, the fluorescence of CellTox™ Green (CTG) and Hoechst 33342 (H) was measured in a standard plate reader.

miR-299-3p Induces Apoptosis in Cancer Cells

Treatment of MDA-MB-231 breast cancer cells with miR-335 had no significant effect of the rate of apoptosis as compared to cells treated with a non-human miR used as negative control (scramble). In stark contrast, treatment with miR-299-3p more than tripled the rate of apoptosis in contrast to the negative control.

```
Sequence listing of precursor and mature
      microRNAs in this application SEQ ID NO 1: >pre-miR-299; MI0000744
AAGAAAUGGUUUACCGUCCCACAUACAUUUUGAAUAUGUAUGUGGGAUGG
UAAACCGCUUCUU SEQ ID NO 2: >miR-299-3p; MIMAT0000687
UAUGUGGGAUGGUAAACCGCUU SEQ ID NO 3: >pre-miR-573; MI0003580;
UUUAGCGGUUUCUCCCUGAAGUGAUGUGUAACUGAUCAGGAUCUACUCAU
GUCGUCUUUGGUAAAGUUAUGUCGCUUGUCAGGGUGAGGAGAGUUUUUG
```

Sequence listing of precursor and mature microRNAs in this application

SEQ ID NO 4: >miR-573; MIMAT0003238
CUGAAGUGAUGUGUAACUGAUCAG

SEQ ID NO 5: >pre-miR-595; MI0003607
ACGGAAGCCUGCACGCAUUUAACACCAGCACGCUCAAUGUAGUCUUGUAA
GGAACAGGUUGAAGUGUGCCGUGGUGUGUCUGGAGGAAGCGCCUGU SEQ ID NO 6: >miR-595; MIMAT0003263
GAAGUGUGCCGUGGUGUGUCU SEQ ID NO 7: >pre-miR-301a-3p; MI0000745
CAGUGCAAUAGUAUUGUCAAAGC SEQ ID NO 8: >miR-301a; MI0000745
ACUGCUAACGAAUGCUCUGACUUUAUUGCACUACUGUACUUUACAGCUAG
CAGUGCAAUAGUAUUGUCAAAGCAUCUGAAAGCAGG SEQ ID NO 9: >pre-mir-671; MI0003760
GCAGGUGAACUGGCAGGCCAGGAAGAGGAGGAAGCCCUGGAGGGGCUGGA
GGUGAUGGAUGUUUUCCUCCGGUUCUCAGGGCUCCACCUCUUUCGGGCCG
UAGAGCCAGGGCUGGUGC SEQ ID NO 10: >miR-671-5p; MIMAT0003880
AGGAAGCCCUGGAGGGGCUGGAG SEQ ID NO 11: >pre-miR-142; MI0000458
GACAGUGCAGUCACCCAUAAAGUAGAAAGCACUACUAACAGCACUGGAGG
GUGUAGUGUUUCCUACUUUAUGGAUGAGUGUACUGUG SEQ ID NO 12: >miR-142-3p; MIMAT0000434
UGUAGUGUUUCCUACUUUAUGGA SEQ ID NO 13: >pre-miR-489; MI0003124
GUGGCAGCUUGGUGGUCGUAUGUGUGACGCCAUUUACUUGAACCUUUAGG
AGUGACAUCACAUAUACGGCAGCUAAACUGCUAC SEQ ID NO 14: >miR-489-3p; MIMAT0002805
GUGACAUCACAUAUACGGCAGC SEQ ID NO 15: >pre-miR-542; MI0003686
CAGAUCUCAGACAUCUCGGGGAUCAUCAUGUCACGAGAUACCAGUGUGCA
CUUGUGACAGAUUGAUAACUGAAAGGUCUGGGAGCCACUCAUCUUCA SEQ ID NO 16: >miR-542-3p; MIMAT0003389
UGUGACAGAUUGAUAACUGAAA SEQ ID NO 17: >pre-miR-506 MI0003193
GCCACCACCAUCAGCCAUACUAUGUGUAGUGCCUUAUUCAGGAAGGUGUU
ACUUAAUAGAUUAAUAUUUGUAAGGCACCCUUCUGAGUAGAGUAAUGUGC
AACAUGGACAACAUUUGGUGGC SEQ ID NO 18: >miR-506-3p; MIMAT0002878
UAAGGCACCCUUCUGAGUAGA SEQ ID NO 19: >pre-miR-494; MI0003134
GAUACUCGAAGGAGAGGUUGUCCGUGUUGUCUUCUCUUUAUUUAUGAUGA
AACAUACACGGGAAACCUCUUUUUUAGUAUC SEQ ID NO 20: >miR-494-3p; MIMAT0002816
UGAAACAUACACGGGAAACCUC SEQ ID NO 21: >pre-miR-26a stemloop; MI0000083
GUGGCCUCGUUCAAGUAAUCCAGGAUAGGCUGUGCAGGUCCCAAUGGGCC
UAUUCUUGGUUACUUGCACGGGACGC SEQ ID NO 22: hsa-miR-26a-5p, MIMAT0000082
UUCAAGUAAUCCAGGAUAGGC SEQ ID NO 23: >pre-miR-326; MI0000808
CUCAUCGUCUGUUGGGCUGGAGGCAGGGCCUUUGUGAAGGCGGGUGGUG
CUCAGAUCGCCUCUGGGCCCUUCCUCCAGCCCCGAGGCGGAUUCA SEQ ID NO 24: >miR-326; MIMAT0000756
CCUCUGGGCCCUUCCUCCAG SEQ ID NO 25: >pre-miR-520c; MI0003158
UCUCAGGCUGUCGUCCUCUAGAGGGAAGCACUUUCUGUUGUCUGAAAGAA
AAGAAAGUGCUUCCUUUUAGAGGGUUACCGUUUGAGA SEQ ID NO 26: >miR-520c-3p; MIMAT0002846
AAAGUGCUUCCUUUUAGAGGGU SEQ ID NO 27: >pre-miR-765; MI0005116
UUUAGGCGCUGAUGAAAGUGGAGUUCAGUAGACAGCCCUUUUCAAGCCCU
ACGAGAAACUGGGGUUUCUGGAGGAGAAGGAAGGUGAUGAAGGAUCUGUU
CUCGUGAGCCUGAA SEQ ID NO 28: >miR-765; MIMAT0003945
UGGAGGAGAAGGAAGGUGAUG SEQ ID NO 29: >pre-miR-376b; MI0002466
CAGUCCUUCUUUGGUAUUUAAAACGUGGAUAUUCCUUCUAUGUUUACGUG
AUUCCUGGUUAAUCAUAGAGGAAAAUCCAUGUUUUCAGUAUCAAAUGCUG SEQ ID NO 30: >miR-376b-3p; MIMAT0002172
AUCAUAGAGGAAAAUCCAUGUU SEQ ID NO 31: >pre-miR-128b; MI0000727
UGUGCAGUGGGAAGGGGGGCCGAUACACUGUACGAGAGUGAGUAGCAGGU
CUCACAGUGAACCGGUCUCUUUCCCUACUGUGUC SEQ ID NO 32: >miR-128-3p; MIMAT0000424
UCACAGUGAACCGGUCUCUUU SEQ ID NO 33: >pre-miR-650; MI0003665
CAGUGCUGGGGUCUCAGGAGGCAGCGCUCUCAGGACGUCACCACCAUGGC
CUGGGCUCUGCUCCUCCUCACCCUCCUCACUCAGGGCACAGGUGAU SEQ ID NO 34: >miR-650; MIMAT0003320
AGGAGGCAGCGCUCUCAGGAC SEQ ID NO 35: >pre-miR-662; MI0003670
GCUGUUGAGGCUGCGCAGCCAGGCCCUGACGGUGGGGUGGCUGCGGGCCU
UCUGAAGGUCUCCCACGUUGUGGCCCAGCAGCGCAGUCACGUUGC SEQ ID NO 36: >miR-662; MIMAT0003325
UCCCACGUUGUGGCCCAGCAG SEQ ID NO 37: >pre-miR-593; MI0003605
CCCCAGAAUCUGUCAGGCACCAGCCAGGCAUUGCUCAGCCCGUUUCCCU
CUGGGGGAGCAAGGAGUGGUGCUGGGUUUGUCUCUGCUGGGGUUUCUCCU SEQ ID NO 38: >miR-593-5p; MIMAT0003261
AGGCACCAGCCAGGCAUUGCUCAGC

---

The invention claimed is:

1. A method of treatment of breast cancer, comprising:
administering to a subject in need thereof a therapeutically effective amount of a nucleic acid molecule consisting essentially of a sequence selected from the group consisting of SEQ ID NO 001 and SEQ ID NO 002,
wherein the nucleic acid molecule initiates apoptosis in cancerous cells, thereby treating the breast cancer.

2. The method of claim 1, wherein the nucleic acid is provided in a pharmaceutical composition additionally comprising polyethylene glycol coupled liposomes, tissue specific antibodies or virus-like particles, cell-penetrating peptides (CPP), penetrating metal particles, magnetic particles, photo activated penetrating particles, chemically activated penetrating particles and enzymatically activated penetrating particle.

3. The method of claim 1, wherein the nucleic acid molecule is provided by a recombinant expression vector.

4. The method of claim 1, wherein the nucleotide sequence is operably linked to a promoter, particularly a promoter operable in a human cell.

* * * * *

SEQUENCE LISTING

<160> NUMBER OF SEQ ID NOS: 38

<210> SEQ ID NO 1
<211> LENGTH: 63
<212> TYPE: RNA
<213> ORGANISM: Homo sapiens

```
<400> SEQUENCE: 1
aagaaauggu uuaccguccc acauacauuu ugaauaugua ugugggaugg uaaaccgcuu    60
cuu                                                                  63

<210> SEQ ID NO 2
<211> LENGTH: 22
<212> TYPE: RNA
<213> ORGANISM: Homo sapiens

<400> SEQUENCE: 2
uaugugggau gguaaaccgc uu                                             22

<210> SEQ ID NO 3
<211> LENGTH: 99
<212> TYPE: RNA
<213> ORGANISM: Homo sapiens

<400> SEQUENCE: 3
uuuagcgguu ucucccugaa gugaugugua acugaucagg aucuacucau gucgucuuug    60
guaaaguuau gucgcuuguc agggugagga gaguuuuug                           99

<210> SEQ ID NO 4
<211> LENGTH: 24
<212> TYPE: RNA
<213> ORGANISM: Homo sapiens

<400> SEQUENCE: 4
cugaagugau guguaacuga ucag                                           24

<210> SEQ ID NO 5
<211> LENGTH: 96
<212> TYPE: RNA
<213> ORGANISM: Homo sapiens

<400> SEQUENCE: 5
acggaagccu gcacgcauuu aacaccagca cgcucaaugu agucuuguaa ggaacagguu    60
gaagugugcc guggugoguc uggaggaagc gccugu                              96

<210> SEQ ID NO 6
<211> LENGTH: 21
<212> TYPE: RNA
<213> ORGANISM: Homo sapiens

<400> SEQUENCE: 6
gaagugugcc guggugoguc u                                              21

<210> SEQ ID NO 7
<211> LENGTH: 23
<212> TYPE: RNA
<213> ORGANISM: Homo sapiens

<400> SEQUENCE: 7
cagugcaaua guauugucaa agc                                            23

<210> SEQ ID NO 8
<211> LENGTH: 86
<212> TYPE: RNA
<213> ORGANISM: Homo sapiens

<400> SEQUENCE: 8
acugcuaacg aaugcucuga cuuuauugca cuacuguacu uuacagcuag cagugcaaua    60
```

```
guauugucaa agcaucugaa agcagg                                            86

<210> SEQ ID NO 9
<211> LENGTH: 118
<212> TYPE: RNA
<213> ORGANISM: Homo sapiens

<400> SEQUENCE: 9
gcaggugaac uggcaggcca ggaagaggag gaagcccugg aggggcugga ggugauggau       60 guuuccucc gguucucagg gcuccaccuc uuucgggccg uagagccagg gcuggugc         118

<210> SEQ ID NO 10
<211> LENGTH: 23
<212> TYPE: RNA
<213> ORGANISM: Homo sapiens

<400> SEQUENCE: 10
aggaagcccu ggaggggcug gag                                               23

<210> SEQ ID NO 11
<211> LENGTH: 87
<212> TYPE: RNA
<213> ORGANISM: Homo sapiens

<400> SEQUENCE: 11
gacagugcag ucacccauaa aguagaaagc acuacuaaca gcacuggagg guguaguguu       60
uccuacuuua uggaugagug uacugug                                           87

<210> SEQ ID NO 12
<211> LENGTH: 23
<212> TYPE: RNA
<213> ORGANISM: Homo sapiens

<400> SEQUENCE: 12
uguaguguuu ccuacuuuau gga                                               23

<210> SEQ ID NO 13
<211> LENGTH: 84
<212> TYPE: RNA
<213> ORGANISM: Homo sapiens

<400> SEQUENCE: 13
guggcagcuu gguggucgua ugugugacgc cauuuacuug aaccuuuagg agugacauca       60
cauauacggc agcuaaacug cuac                                              84

<210> SEQ ID NO 14
<211> LENGTH: 22
<212> TYPE: RNA
<213> ORGANISM: Homo sapiens

<400> SEQUENCE: 14
gugacaucac auauacggca gc                                                22

<210> SEQ ID NO 15
<211> LENGTH: 97
<212> TYPE: RNA
<213> ORGANISM: Homo sapiens

<400> SEQUENCE: 15
cagaucucag acaucucggg gaucaucaug ucacgagaua ccagugugca cuugugacag       60
```

```
auugauaacu gaaaggucug ggagccacuc aucuuca                                    97

<210> SEQ ID NO 16
<211> LENGTH: 22
<212> TYPE: RNA
<213> ORGANISM: Homo sapiens

<400> SEQUENCE: 16
ugugacagau ugauaacuga aa                                                   22

<210> SEQ ID NO 17
<211> LENGTH: 124
<212> TYPE: RNA
<213> ORGANISM: Homo sapiens

<400> SEQUENCE: 17
gccaccacca ucagccauac augucuagu gccuuauuca ggaagguguu acuuaauaga            60
uuaauauuug uaaggcaccc uucugaguag aguaaugugc aacauggaca acauuugugg         120
uggc                                                                      124

<210> SEQ ID NO 18
<211> LENGTH: 21
<212> TYPE: RNA
<213> ORGANISM: Homo sapiens

<400> SEQUENCE: 18
uaaggcaccc uucugaguag a                                                    21

<210> SEQ ID NO 19
<211> LENGTH: 81
<212> TYPE: RNA
<213> ORGANISM: Homo sapiens

<400> SEQUENCE: 19
gauacucgaa ggagagguug uccguguugu cuucucuuua uuuaugauga aacauacacg           60
ggaaaccucu uuuuaguau c                                                     81

<210> SEQ ID NO 20
<211> LENGTH: 22
<212> TYPE: RNA
<213> ORGANISM: Homo sapiens

<400> SEQUENCE: 20
ugaaacauac acgggaaacc uc                                                   22

<210> SEQ ID NO 21
<211> LENGTH: 77
<212> TYPE: RNA
<213> ORGANISM: Homo sapiens

<400> SEQUENCE: 21
guggccucgu ucaaguaauc caggauaggc ugugcagguc ccaaugggcc uauucuuggu           60
uacuugcacg gggacgc                                                         77

<210> SEQ ID NO 22
<211> LENGTH: 21
<212> TYPE: RNA
<213> ORGANISM: Homo sapiens

<400> SEQUENCE: 22
uucaaguaau ccaggauagg c                                                    21
```

<210> SEQ ID NO 23
<211> LENGTH: 95
<212> TYPE: RNA
<213> ORGANISM: Homo sapiens

<400> SEQUENCE: 23
cucaucuguc uguugggcug gaggcagggc cuuugugaag gcgggguggug cucagaucgc    60 cucugggccc uuccuccagc cccgaggcgg auuca                                95

<210> SEQ ID NO 24
<211> LENGTH: 20
<212> TYPE: RNA
<213> ORGANISM: Homo sapiens

<400> SEQUENCE: 24
ccucugggcc cuuccuccag                                                 20

<210> SEQ ID NO 25
<211> LENGTH: 87
<212> TYPE: RNA
<213> ORGANISM: Homo sapiens

<400> SEQUENCE: 25
ucucaggcug ucguccucua gagggaagca cuuucuguug ucugaaagaa agaaagugc      60 uuccuuuuag aggguuaccg uuugaga                                         87

<210> SEQ ID NO 26
<211> LENGTH: 22
<212> TYPE: RNA
<213> ORGANISM: Homo sapiens

<400> SEQUENCE: 26
aaagugcuuc cuuuuagagg gu                                              22

<210> SEQ ID NO 27
<211> LENGTH: 114
<212> TYPE: RNA
<213> ORGANISM: Homo sapiens

<400> SEQUENCE: 27
uuuaggcgcu gaugaaagug gaguucagua gacagcccuu uucaagcccu acgagaaacu     60
gggguuucug gaggagaagg aaggugauga aggaucuguu cucgugagcc ugaa          114

<210> SEQ ID NO 28
<211> LENGTH: 21
<212> TYPE: RNA
<213> ORGANISM: Homo sapiens

<400> SEQUENCE: 28
uggaggagaa ggaaggugau g                                               21

<210> SEQ ID NO 29
<211> LENGTH: 100
<212> TYPE: RNA
<213> ORGANISM: Homo sapiens

<400> SEQUENCE: 29
caguccuucu uugguauuua aaacguggau auuccuucua uguuuacgug auuccugguu     60
aaucauagag gaaaauccau guuuucagua ucaaaugcug                          100

```
<210> SEQ ID NO 30
<211> LENGTH: 22
<212> TYPE: RNA
<213> ORGANISM: Homo sapiens

<400> SEQUENCE: 30
aucauagagg aaaauccaug uu                                              22

<210> SEQ ID NO 31
<211> LENGTH: 84
<212> TYPE: RNA
<213> ORGANISM: Homo sapiens

<400> SEQUENCE: 31
ugugcagugg gaagggggc cgauacacug uacgagagug aguagcaggu cucacaguga      60
accggucucu uucccuacug uguc                                            84

<210> SEQ ID NO 32
<211> LENGTH: 21
<212> TYPE: RNA
<213> ORGANISM: Homo sapiens

<400> SEQUENCE: 32
ucacagugaa ccggucucuu u                                               21

<210> SEQ ID NO 33
<211> LENGTH: 96
<212> TYPE: RNA
<213> ORGANISM: Homo sapiens

<400> SEQUENCE: 33
cagugcuggg gucucaggag gcagcgcucu caggacguca ccaccauggc cugggcucug     60
cuccuccuca cccuccucac ucagggcaca ggugau                               96

<210> SEQ ID NO 34
<211> LENGTH: 21
<212> TYPE: RNA
<213> ORGANISM: Homo sapiens

<400> SEQUENCE: 34
aggaggcagc gcucucagga c                                               21

<210> SEQ ID NO 35
<211> LENGTH: 95
<212> TYPE: RNA
<213> ORGANISM: Homo sapiens

<400> SEQUENCE: 35
gcuguugagg cugcgcagcc aggcccugac ggugggugg cugcgggccu ucugaagguc      60
ucccacguug uggcccagca gcgcagucac guugc                                95

<210> SEQ ID NO 36
<211> LENGTH: 21
<212> TYPE: RNA
<213> ORGANISM: Homo sapiens

<400> SEQUENCE: 36
ucccacguug uggcccagca g                                               21

<210> SEQ ID NO 37
<211> LENGTH: 100
```

```
<212> TYPE: RNA
<213> ORGANISM: Homo sapiens

<400> SEQUENCE: 37
cccccagaau cugucaggca ccagccaggc auugcucagc ccguuucccu cuggggagc      60 aaggaguggu gcuggguuug ucucugcugg gguuucuccu                          100

<210> SEQ ID NO 38
<211> LENGTH: 25
<212> TYPE: RNA
<213> ORGANISM: Homo sapiens

<400> SEQUENCE: 38
aggcaccagc caggcauugc ucagc                                           25
```